(12) United States Patent
Gebauer (10) Patent No.: US 9,663,753 B2
(45) Date of Patent: May 30, 2017

(54) TANGENTIAL FLOW PERFUSION SYSTEM

(71) Applicant: GE Healthcare Bio-Sciences AB, Uppsala (SE)

(72) Inventor: Klaus Gebauer, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 14/430,346

(22) PCT Filed: Sep. 25, 2013

(86) PCT No.: PCT/SE2013/051110
§ 371 (c)(1),
(2) Date: Mar. 23, 2015

(87) PCT Pub. No.: WO2014/051503
PCT Pub. Date: Apr. 3, 2014

(65) Prior Publication Data
US 2015/0247114 A1    Sep. 3, 2015

(30) Foreign Application Priority Data
Sep. 27, 2012 (SE) ........................ 1251091

(51) Int. Cl.
*C12M 1/00* (2006.01)
*C12N 1/00* (2006.01)
(Continued)

(52) U.S. Cl.
CPC ............. *C12M 29/10* (2013.01); *B01D 61/18* (2013.01); *B01D 61/22* (2013.01); *B01D 63/02* (2013.01);
(Continued)

(58) Field of Classification Search
CPC .......... B01D 2313/243; B01D 2321/04; B01D 63/02; B01D 61/22; B01D 65/02;
(Continued)

(56) References Cited

U.S. PATENT DOCUMENTS 6,511,124 B2    1/2003  Combs
6,544,424 B1    4/2003  Shevitz
(Continued)

FOREIGN PATENT DOCUMENTS

CN    103298538 A    9/2013
CN    104593277 A    5/2015
(Continued)

OTHER PUBLICATIONS

Haidong Zhou et al., "Separation of hyaluronic acid from fermentation broth by tangential flow microfiltration and ultrafiltration," Separation and Purification Technology, vol. 52, Issue 1., pp. 29-38, 2006.

(Continued)

*Primary Examiner* — Michael Hobbs
(74) *Attorney, Agent, or Firm* — Wood IP LLC (57) ABSTRACT

The invention discloses a system for perfusion culture of cells which comprises: a bioreactor; a filter unit with a retentate inlet end, a retentate outlet end and a permeate outlet port; a reciprocating pump fluidically connected to the retentate inlet end, with the retentate inlet end fluidically connected to the bioreactor via an inlet check valve arranged to allow flow in the direction from the bioreactor to the retentate inlet end and to block flow in the reverse direction, and where the retentate outlet end is fluidically connected to the bioreactor via an outlet check valve arranged to allow flow in the direction from the retentate outlet end to the bioreactor and to block flow in the reverse direction; and where the inlet and outlet check valves are each fluidically (Continued)

connected to a tubing branch point, which is further connected to the bioreactor via a length of tubing. In an alternative embodiment, each of said inlet and outlet check valves is fluidically connected to the bioreactor via separate lengths of tubing. The invention further discloses a pre-sterilized system for perfusion culture of cells which comprises: a bioreactor; a reciprocating pump and a filter unit fluidically connected to the reciprocating pump and fluidically connected to the bioreactor via at least one aseptic connector.

39 Claims, 4 Drawing Sheets

(51) Int. Cl.
*C12M 1/34* (2006.01)
*B01D 61/22* (2006.01)
*B01D 63/02* (2006.01)
*B01D 65/02* (2006.01)
*B01D 61/18* (2006.01)
*B01D 63/08* (2006.01)

(52) U.S. Cl.
CPC ............ *B01D 63/08* (2013.01); *B01D 65/02* (2013.01); *C12M 29/02* (2013.01); *C12M 29/04* (2013.01); *C12M 29/12* (2013.01); *C12M 29/16* (2013.01); *C12M 29/18* (2013.01); *C12M 41/00* (2013.01); *C12M 41/40* (2013.01); *C12M 47/10* (2013.01); *B01D 2313/243* (2013.01); *B01D 2313/44* (2013.01); *B01D 2321/04* (2013.01)

(58) Field of Classification Search
CPC ...... C12M 29/02; C12M 29/04; C12M 29/10; C12M 29/16; C12M 29/18; C12M 41/00; C12M 41/40; C12M 47/10
See application file for complete search history.

(56) References Cited

U.S. PATENT DOCUMENTS

| | | | |
|---|---|---|---|
| 8,501,460 | B2 | 8/2013 | Furey |
| 2004/4259240 | | 12/2004 | Fadden |
| 2009/0042253 | A1 | 2/2009 | Hiller |
| 2011/0111486 | A1* | 5/2011 | Furey .................... C12M 23/28 435/287.1 |
| 2013/0270165 | A1 | 10/2013 | Shevitz |
| 2014/0087424 | A1 | 3/2014 | Crowley et al. |

FOREIGN PATENT DOCUMENTS

| | | |
|---|---|---|
| EP | 1354941 | 10/2003 |
| GB | 2225789 | 6/1990 |
| WO | 2005007269 | 1/2005 |
| WO | 2012026978 | 3/2012 |
| WO | 2012077742 | 6/2012 |

OTHER PUBLICATIONS

Chinese Search Report in corresponding CN Appl. No. 201380050422.3, filed Sep. 25, 2013. (In English Translation).
Chinese Office Action in corresponding CN Appl. No. 201380050422.3, filed Sep. 25, 2013. (In English Translation).
Zhou et al., "Separation of hyaluronic acid from fermentation broth by tangential flow microfiltration and ultrafiltration", Separation and Purification Technology, 52:29-38 (2006).

* cited by examiner

TANGENTIAL FLOW PERFUSION SYSTEM

TECHNICAL FIELD OF THE INVENTION

The present invention relates to bioreactor systems, and more particularly to bioreactor systems for perfusion culture with a reciprocating pump. The invention also relates to methods of perfusion culture of cells.

BACKGROUND OF THE INVENTION

Cell culture has generated considerable interest in recent years due to the revolution in genetic engineering and biotechnology. Cells are cultured to make for example proteins, receptors, vaccines, and antibodies for therapy, research, and for diagnostics.

It has long been recognized that perfusion culture offers relatively good economics for cell cultures. In this operation, cells are retained in the bioreactor, and the product is continuously removed along with toxic metabolic byproducts. Feed, containing nutrients, is added continually to the bioreactor. Perfusion culture operation is capable of achieving high cell densities and more importantly, the cells can be maintained in a highly productive state for weeks. This achieves much higher yields and reduces the size of the bioreactor necessary. It is also a useful technique for cultivating primary or other slow growing cells.

Perfusion operations have been greatly developed during recent years. U.S. Pat. No. 6,544,424 discloses a perfusion system where a reciprocating diaphragm pump during the outward stroke pulls culture liquid from the bioreactor through a hollow fiber filter and during the inward stroke pushes the liquid back through the filter to the bioreactor. During the outward stroke, permeate is generated and during the inward stroke, the filter is backflushed to reduce the clogging by cells. Further developments of this technology are described in WO 2012/026978, relating to incorporation of the bioreactor and the perfusion unit into a single apparatus and in US 2011/0111486, where the flow to and from the perfusion unit is also used to provide additional agitation in the bioreactor. However, the filtration efficiency of these systems is not optimal, and they are still sensitive to clogging and fouling of the membranes.

Accordingly there is a need for improved designs of perfusion systems, allowing better control of the filtration.

SUMMARY OF THE INVENTION

One aspect of the invention is to provide a perfusion system with improved control of the filtration. This is achieved with a system as defined in claim 1.

One advantage is that clogging and fouling can be prevented. Further advantages are that the system is scalable, that it is compatible with bioreactors of the rocking type and that the perfusion unit can easily be accommodated as a contained unit within an integral housing.

A second aspect of the invention is to provide a method for perfusion culture allowing improved filtration control. This is achieved with a method as defined in the claims.

A third aspect of the invention is to provide a pre-sterilized perfusion system. This is achieved with a system as defined in the claims.

Further suitable embodiments of the invention are described in the dependent claims.

DEFINITIONS

DETAILED DESCRIPTION OF EMBODIMENTS

In one aspect the present invention discloses a system 1;31;51 for perfusion culture of cells.

The system comprises:
 a) at least one bioreactor 2;32;52;
 b) at least one filter unit 3;33;53 which has a retentate inlet end 4;34;54, a retentate outlet end 5;35;55 and at least one permeate outlet port 6;36;56 and;
 c) at least one reciprocating pump 7;37;57 which is fluidically connected to the retentate inlet end.

The retentate inlet end is fluidically connected to the bioreactor via an inlet check valve 8;38;58 which is arranged to allow flow in the direction from the bioreactor to the retentate inlet end and to block flow in the reverse direction. The retentate outlet end is fluidically connected to the bioreactor via an outlet check valve 9;39;59 which is arranged to allow flow in the direction from the retentate outlet end to the bioreactor and to block flow in the reverse direction.

Further, the inlet and outlet check valves are each fluidically connected to a tubing branch point 10;40;60, which is also connected to the bioreactor via a length of tubing 11;41;61, e.g. a length of flexible tubing. Suitably, the connection between the tubing branch point and the bioreactor is via a single length of tubing. This is convenient as it minimizes the number of ports needed in the bioreactor and it reduces the complexity of the tubing package around the bioreactor. The latter is particularly important for moving bioreactors, e.g. of the rocking bag type, where the number of moving tubes needs to be kept at a minimum. An alternative possibility is however to have each of the the inlet 8;38;58 and outlet 9;39;59 check valves fluidically connected to the bioreactor via separate lengths of tubing (not shown), without the branch point 10;40;60. Separate tubing for inlet and outlet can ensure the favorable condition that liquid in tubing in between the bioreactor and the device is processed solely in a single pass regardless of the ratio between processed volume (difference between volume in inward and outward stroke of the pump) to the holdup volume in tubing in between bioreactor and device. Another alternative is to position the branch point at an intermediate position along the fluid connection between bioreactor and device, hereby accounting for process and hold up volumes and optimizing performance.

The bioreactor can suitably comprise a vessel with an inner volume 12;48;62 and agitation means (not shown) located inside and/or outside the inner volume. The agitation means can e.g. be an impeller inside the inner volume, driven directly or magnetically by a motor outside the inner volume. The agitation means can also be a movable support on which the vessel is resting, which can convey a rocking and/or oscillatory movement to the vessel.

Figure 2:
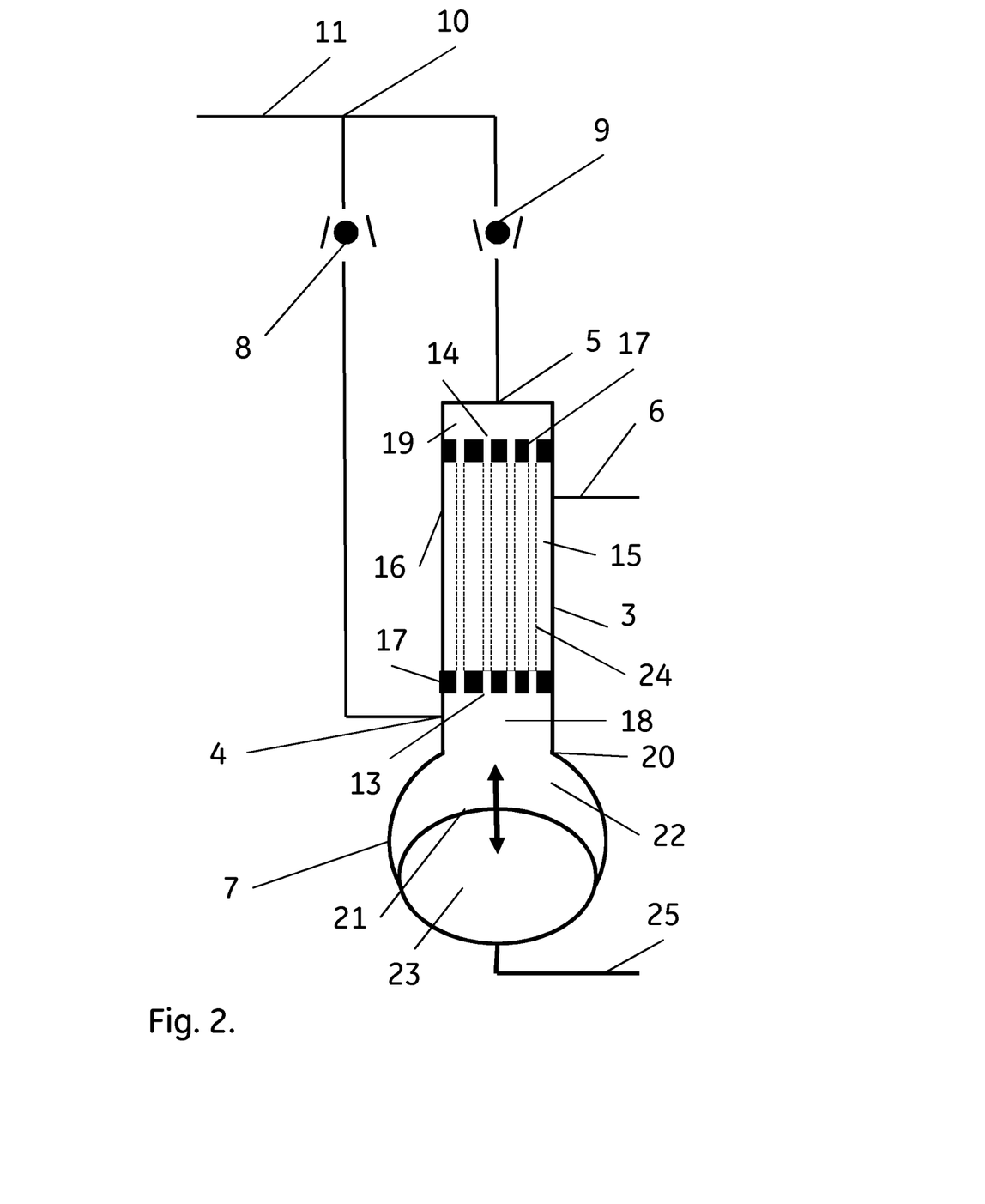
FIG. 2 shows an enlarged view of the filter unit, pump and fluid connectors of the system shown in FIG. 1.

The filter unit can be a filter adapted for tangential flow filtration, e.g. a hollow fiber cartridge or a flat sheet cassette, with a plurality of membranes delimiting a retentate side and a permeate side. When the filter unit is a hollow fiber cartridge, as illustrated in FIG. 2, the retentate inlet end can be adjacent and in connection with the fiber lumens 13 at one end of a hollow fiber bundle and the retentate outlet end can be adjacent and in connection with the fiber lumens 14 at the other end of the hollow fiber bundle. In this case, the permeate outlet port can be connected to the volume surrounding the shell side of the hollow fibers 24 in the bundle—the permeate compartment 15, which volume is sealed off from the fiber lumens of the bundle. The filter unit can also comprise two permeate outlet ports, in which case it is possible to circulate the permeate along the fibers in the permeate compartment, suitably in a countercurrent (opposite) direction to the retentate circulation direction through the lumens. The filter unit can be contained in an elongated (e.g. cylindrical) housing 16 with the hollow fiber bundle located in the central part of the housing, and seals 17 delimiting the permeate compartment 15 from a retentate inlet compartment 18 and a retentate outlet compartment 19. The retentate inlet compartment may be directly connected to the reciprocating pump at a joint 20.

Figure 1:
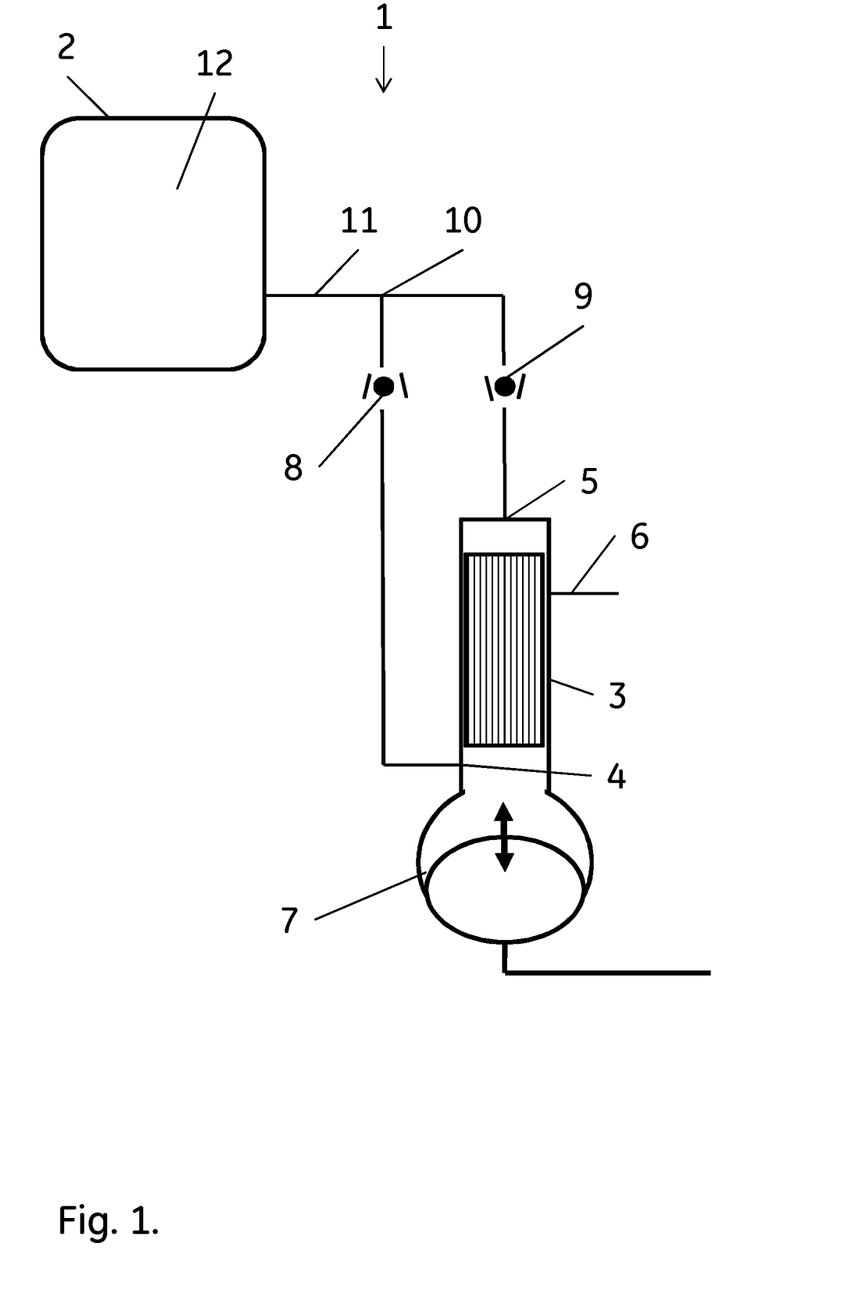
FIG. 1 shows a perfusion system according to the invention.
Figure 3:
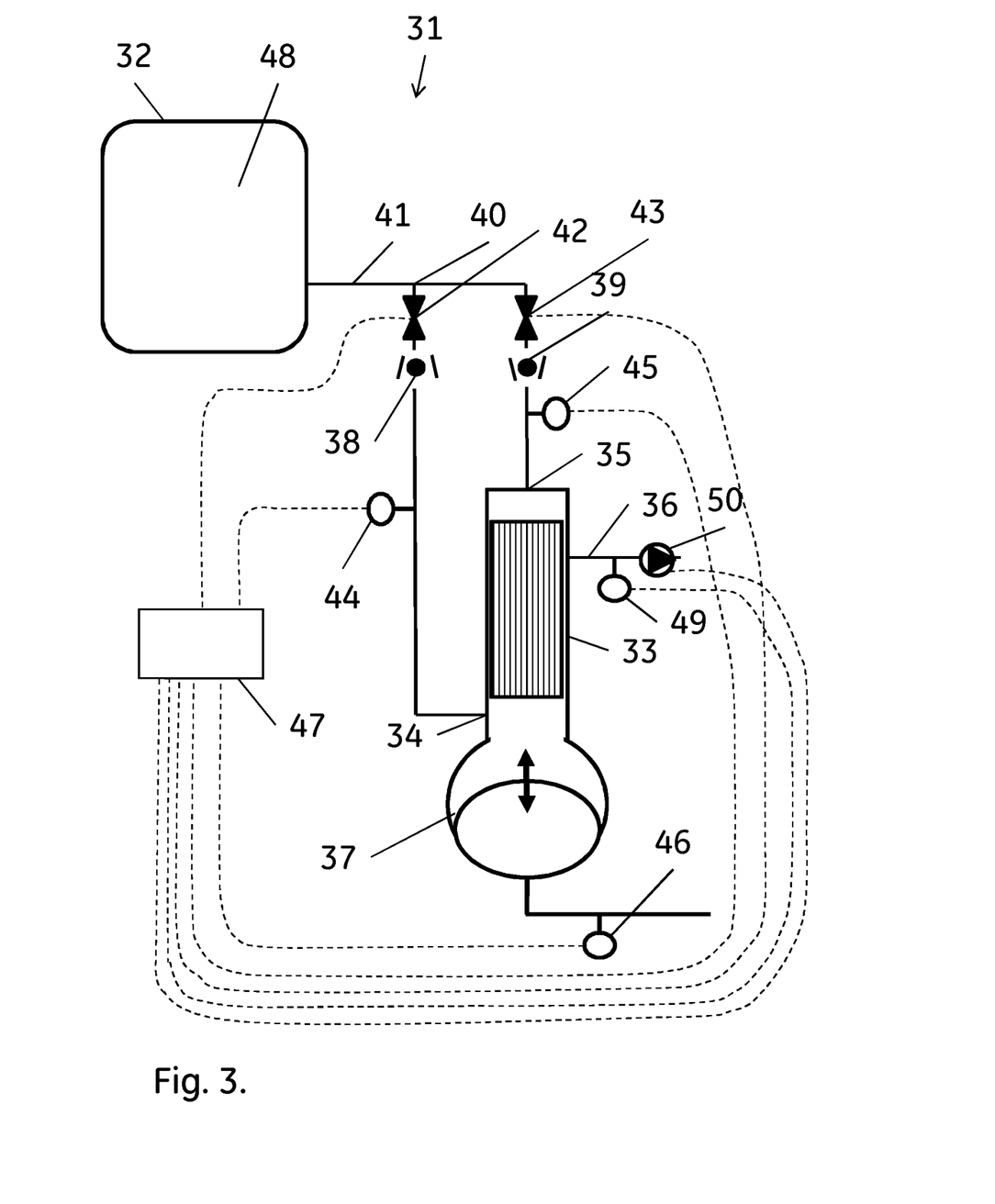
FIG. 3 shows a perfusion system according to the invention with control valves, pressure transducers and control unit.

The reciprocating pump can suitably comprise a reciprocating moving member 21, such as e.g. a diaphragm, a membrane or a piston. The reciprocating moving member can move back and forth in relation to a pump chamber 22 (also called a cylinder, when the moving member is a piston), forcing fluid (e.g. culture liquid) out from the pump chamber during an inward stroke of the moving member and sucking fluid (e.g. culture liquid) into the pump chamber during an outward stroke. The stroke volume of the reciprocating pump corresponds to the fluid (culture liquid) volume displaced out from or into the pump chamber during each stroke. The reciprocating pump may e.g. be a fluid-driven diaphragm pump as illustrated in FIGS. 1-3, with a pump chamber 22 and a drive fluid-filled drive chamber 23 separated by a flexible diaphragm 21, which constitutes the reciprocating moving member. The drive fluid can be a gas, e.g. air, or a liquid. When fluid pressure is applied to the drive chamber via a drive fluid supply line 25, the diaphragm expels liquid from the pump chamber in an inward stroke and when the fluid pressure is released, the diaphragm flexes back and draws liquid into the pump chamber in an outward stroke. The pump chamber may e.g. be directly connected to the retentate inlet compartment of the filter unit at a joint 20. Alternatively, it may be connected via a fluid connector (not shown), such as a short piece of tubing with a diameter large enough not to impede the liquid flow and a volume significantly smaller than the stroke volume of the reciprocating pump (e.g. less than 20% of the stroke volume, such as less than 10% or less than 5% of the stroke volume), optionally via an aseptic connector.

The connection between the retentate inlet end and the branch point, as well as between the retentate outlet end and the branch point can be achieved e.g. by tubing, such as flexible tubing, with the inlet and outlet check valves in-line with the tubing or adjacent the branch point or the inlet/outlet ends. The branch point 10;40;60 may be e.g. a three-way tubing connector or a manifold. The connection between the branch point and the bioreactor may be a single line in the form of a length of tubing 11;41;61, such as flexible tubing. The tubing length may be connected to the inner volume of the bioreactor vessel through a port in the vessel wall. The inlet and outlet check valves may be of any suitable check valve type, e.g. flap, ball, slit disk valves etc.

During the outward stroke of the reciprocating pump, culture liquid will be drawn from the bioreactor via the length of tubing 11,41;61 and the branch point 10;40;60 to the retentate inlet end 4;34;54 of the filter unit 3;33;53. At the same time, the outward stroke generates a negative pressure on the retentate side of the filter unit, which causes a certain amount of permeate to backflush the filter membrane and thus clean the membrane from clogged cells and other material. During the inward stroke of the reciprocating pump, culture liquid is pushed through the retentate side of the filter unit, producing permeate that can be withdrawn, and further via the retentate outlet end 5;35;55, the branch point 10;40;60 and the length of tubing 11;41;61 back to the bioreactor. This flow routing has a number of advantages in comparison with the previously disclosed routings:

i) Possibility for individual pressure control during the inward and outward strokes. During the outward stroke, the negative pressure can be controlled to avoid outgassing and bubble formation and to optimize the backflushing. During the inward stroke, the transmembrane pressure over the filter unit can be optimized to maximize the mass transport over the filter membrane. The latter is particularly important when the filter unit comprises an ultrafiltration membrane for removal of metabolites as discussed below, but it is also important to reduce fouling and clogging when the filter unit comprises a microfiltration membrane. The individual control further allows for perfusion cultivation methods with minimal mechanical damage to cells and/or sensitive proteins, as well as for generally improving robustness and reproducibility.

ii) The individual pressure control also provides possibility for new methods with combinations, variations and control of flows and pressures. One example is that an inlet control valve (as discussed below) can be used to throttle the flow to the retentate inlet end and in combination with a slow outward stroke of the reciprocating pump generate a very long backflush cycle.

iii) The backflush becomes even and well-controlled due to the essentially constant pressure differential over the membrane during the outward stroke.

iv) Scalability of the system is strongly improved as the pressures and pressure differentials over the membrane can be kept constant regardless of tubing diameters and lengths as well as the pressure inside the bioreactor and the hydrostatic pressure due to the vertical distance between the bioreactor and the filter unit.

The construction materials used in the system can suitably be compatible with commonly used sterilization methods, such as e.g. gamma irradiation and/or autoclaving. For reusable components, stainless steel (e.g. with corrosion resistance at least equivalent to 316 L) or engineering plastics such as polysulfone, PEEK etc may be used, while for single-use components, plastics, such as e.g. polysulfone, polypropylene, polyethylene or ethylene copolymers, may be used.

To avoid infection of the cell culture, the bioreactor and all components in contact with the culture fluid are suitable sterilized before cultivation. The system or parts of the system may be assembled and sterilized by autoclaving or radiation, or one or more components may be presterilized and assembled in a sterile system. To facilitate assembly, the sterilized system parts or components may be equipped with aseptic connectors, e.g. of the ReadyMate type (GE Healthcare). Alternatively, the sterilized system parts/components may be contained in aseptic packages and assembled in a sterile clean room.

In some embodiments, the length of tubing 11;41;61 has an inner volume lower than or equal to 50%, such as lower than or equal to 20% or 10%, of the stroke volume of the reciprocating pump. This has the advantage that a major part of the stroke volume is utilized for transport of liquid from the bioreactor and back via the filter unit.

In some embodiments, the permeate outlet port 36 is connected to a permeate pump 50. The permeate pump can be used to withdraw permeate from the filter unit and can also be utilized for control of the transmembrane pressure in the filter unit. The permeate pump may e.g. be a peristaltic pump. The permeate pump 50 can be arranged to operate in two flow directions, e.g. in a forward direction conveying permeate from the permeate outlet to a storage or waste vessel (not shown) or to further processing operations (not shown) and in a backward direction for backflushing the filter membrane with permeate.

Figure 4:
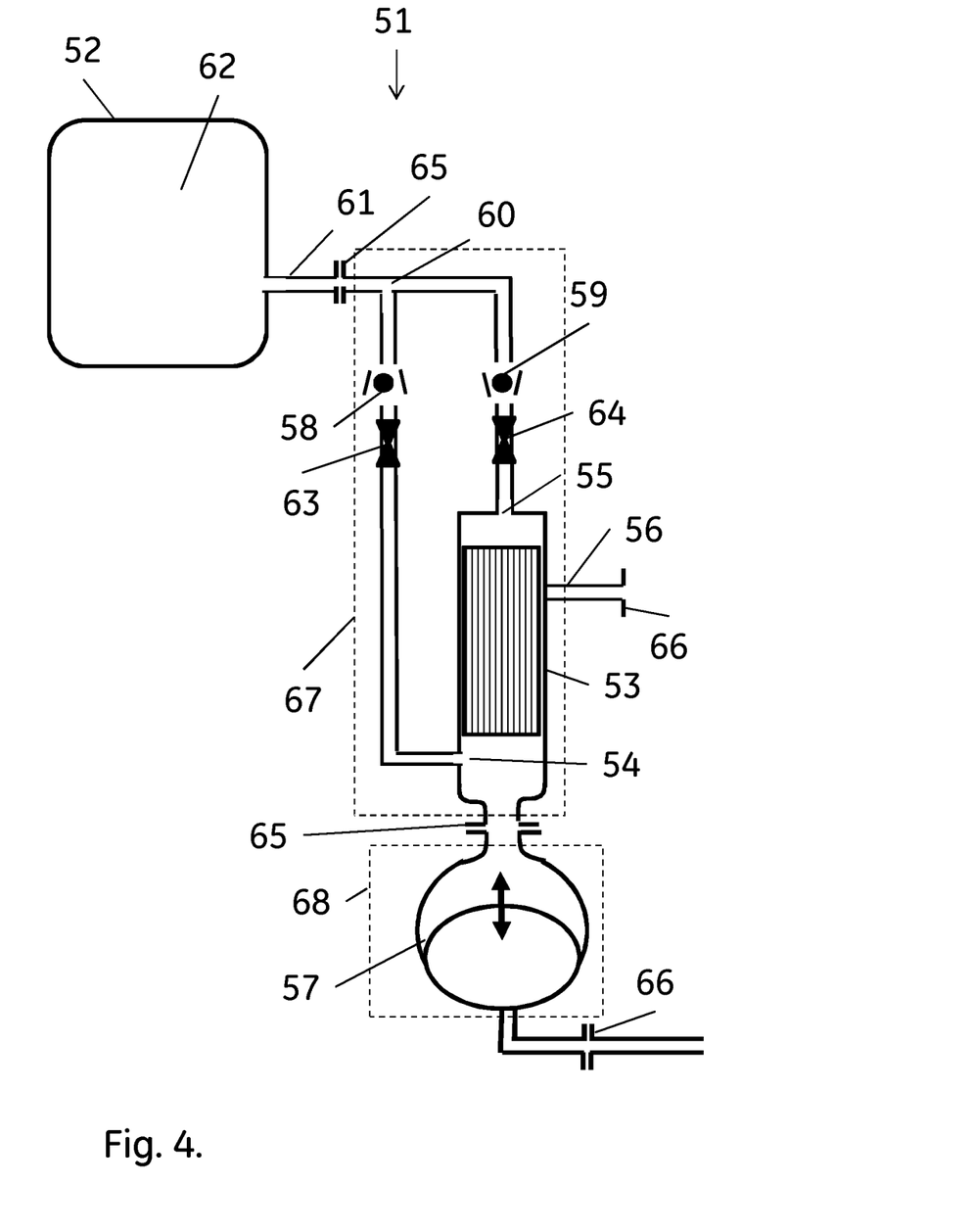
FIG. 4 shows a perfusion system according to the invention, with aseptic connectors and unit housings.

In certain embodiments, illustrated by FIGS. 3 and 4, the system comprises an inlet control valve 42;63 between the retentate inlet end 34;54 and the branch point 40;60. It can be located either between the retentate inlet end and the inlet check valve or between the inlet check valve and the branch point. It can also form an integrated part of the inlet check valve. The inlet control valve can suitably be capable of adjusting the flow and/or the pressure drop over the fluid connection between the bioreactor and the retentate inlet end.

In some embodiments, illustrated by FIGS. 3 and 4, the system comprises an outlet control valve 43;64 between the retentate outlet end 35;55 and the branch point 40;60. It can be located either between the retentate outlet end and the retentate outlet check valve or between the retentate outlet check valve and the branch point. It can also form an integrated part of the outlet check valve or one or more check valve(s) may be combined with one or more control valve(s) in an integrated valve block. The outlet control valve can suitably be capable of adjusting the flow and/or the pressure drop over the fluid connection between the retentate outlet end and the bioreactor. The inlet and outlet control valves can be any type of valve suitable for adjusting liquid flow and they can also be clamping devices applied on the outside of flexible tubing, e.g. pinch valves, hose closure clamps etc. The control valves can be either manually adjustable or arranged to be adjustable according to signals transmitted from a control unit. Such signals can e.g. be of electrical, electromagnetic, optical or pneumatic character.

In certain embodiments, illustrated by FIG. 3, the system comprises an inlet pressure transducer 44 arranged to measure the pressure at the retentate inlet end. This pressure transducer can be located at the retentate inlet end of the filter unit 33 or at any point between the retentate inlet end and the inlet control valve. In embodiments without inlet control valve, it can be located at any point between the retentate inlet end and the branch point. The system can also (or alternatively) comprise an outlet pressure transducer 45 arranged to measure the pressure at the retentate outlet end. This pressure transducer can be located at the retentate outlet end of the filter unit 33 or at any point between the retentate outlet end and the outlet control valve. In embodiments without outlet control valve, it can be located at any point between the retentate outlet end and the branch point. The pressure transducers can be either manually readable manometers or transducers arranged to transmit pressure data to a control unit, e.g. by electrical, electromagnetic or optical means. The outlet pressure transducer 45 can e.g. be employed for an exact determination of the transmembrane pressure over the filter unit and membrane, respectively.

In some embodiments, the permeate outlet port 36 comprises a permeate pressure transducer 49. The permeate pressure transducer can be capable of measuring the pressure on the permeate side of the filter unit, which in combination with data from the inlet and/or outlet pressure transducers can be used to calculate the transmembrane pressure over the filter unit. The permeate pressure transducer can also be used in a feedback loop for control of the transmembrane pressure by the operation of the permeate pump 50 or by some other permeate pressure control means (e.g. hydrostatic pressure control). Transducer 49 is also useful for control of the backflush cycle during the outward stroke of the reciprocating pump.

In some embodiments, illustrated by FIG. 3, the reciprocating pump 37 is a fluid-driven diaphragm pump and the system comprises a drive fluid pressure transducer 46 arranged to measure the drive fluid pressure in the reciprocating pump, mounted e.g. in the drive fluid supply line. The drive fluid pressure transducer can be either a manually readable manometer or a transducer arranged to transmit pressure data to a control unit, e.g. by electrical, electromagnetic or optical means. The drive fluid can be a gas (e.g. air) or a liquid.

In certain embodiments, the reciprocating pump 37 is a gas-driven diaphragm pump and the system comprises a gas pressure transducer 46 arranged to measure the gas pressure in the pump, mounted e.g. in the gas supply line. The gas can in particular be air, in which case the gas (drive fluid) supply is a source of compressed air.

In some embodiments, the reciprocating pump 7;37;57 is designed as a diaphragm pump with a highly flexible diaphragm, e.g. a soft silicone rubber diaphragm, hereby reducing mechanical energy loss between the reciprocating pump at the side of the fluid supply line towards the side of the filter unit 3;33;53 and its retentate inlet end 4;34;54. Hereby, the pressure at the inlet side of the filter unit 33 will be equal to the pressure measured at the pressure transducer at the side of the fluid supply line 46. Thus, the fluid pressure of the bioreactor fluid at the side of the retentate inlet, and hereby the filtration process and the transmembrane pressure, can effectively be measured and controlled by employing the drive fluid pressure transducer 46, which is not in contact with the bioreactor fluid. This design gives advantages when designing a system with single-use components in contact with the bioreactor fluid. It reduces cost and complexity as the drive fluid pressure transducer 46 can be re-usable and does not need to be sterilized. Hence also non-sterilizable high performance sensors can be used and if a sterilizable high performance sensor is used it does not need to be recalibrated after sterilization.

In certain embodiments, illustrated by FIG. 3, the system comprises at least one control unit 47, arranged to control at least one of the reciprocating pump and the inlet and outlet control valves depending on pressure data received from at least one of the inlet and outlet pressure transducers. The control unit(s) can suitably be electrically, electromagnetically (e.g. by wireless communication), optically (e.g. via optical fibers) or pneumatically connected to at least one of the reciprocating pump and the inlet and outlet control valves and to at least one of the inlet and outlet pressure transducers. The control unit(s) can be e.g. a computer, a programmable logic controller or any similar device capable of a) receiving input signals from one or more pressure transducers, b) calculating one or more output parameters from the input signals according to a predetermined method and c) transmitting the output parameter(s) as a signal/signals to one or more control valves and/or a pump. The control unit can be one integrated control unit, arranged to control both the reciprocating pump and the inlet and/or the outlet control valve or the system may comprise a main control unit (or a valve control unit) and a pump control unit (not shown). The pump control unit may be e.g. be arranged to control the flow and pressure profile generated by the reciprocating pump via one or more of the stroke frequency, the stroke length and the velocity of the moving member during the inward and outward strokes. In the case of a fluid driven diaphragm pump, the stroke frequency, the stroke length and the diaphragm velocity can be controlled e.g. via one or more valves on the drive fluid supply line. As noted above, the features of the pump control unit can also be integrated into a main control unit, or—vice versa—the control valve(s) may also be controlled by an integrated pump control unit. Alternatively, the control valve(s) can be preset or manually adjusted, such that only a pump control unit is needed.

The control unit may also be connected to the permeate pump 50 and/or the permeate pressure transducer 49 for control of the transmembrane pressure.

In some embodiments the filter unit is a hollow fiber cartridge or a flat sheet cassette. Hollow fiber cartridges have been described above, but it is also possible to use a flat sheet cassette of the conventional tangential flow filtration type. In this case, the retentate inlet apertures correspond to the fiber lumen ends on the retentate inlet side, the retentate outlet apertures to the lumen ends on the retentate outlet side and the permeate apertures to the permeate outlet.

In certain embodiments the bioreactor comprises an inflatable flexible bag, resting on a movable support, and the length of tubing 11;41;61 is a flexible length of tubing. The system of the invention is particularly suitable for bioreactors which are agitated by moving the entire bioreactor vessel (i.e. the inflatable flexible bag), since only one length of tubing is needed to connect to the bioreactor, which keeps the number of moving connections to the vessel low and reduces entangling of these.

In some embodiments, the system is partially or entirely composed of single-use components, which can suitable be presterilized e.g. by gamma irradiation or autoclaving and then connected together using aseptic connectors, such as e.g. ReadyMate (GE Healthcare). One example of such a system 51 is illustrated in FIG. 4, with aseptic connectors 65 and connectors which may or may not be aseptic 66. As indicated in FIG. 4. it is also possible to contain the filter unit 53, check valves 58,59 and control valves 63,64, as well as inlet and outlet pressure transducers (not shown), in an outer housing 67. It is also possible to contain the reciprocating pump 57 in the same housing or in a separate housing 68. The reciprocating pump 57 may be single-use or reusable and it may even be assembled from a single use part comprising the pump chamber and the diaphragm and a reusable part comprising the drive chamber and the drive fluid supply line with the drive fluid pressure transducer. The single use part of the reciprocating pump may in this case also be integrated with the filter unit.

Although the figures show the reciprocating pump 7;37; 57 placed below the filter unit 3;33;53, other orientations are equally possible, e.g. by placing the reciprocating pump above the filter unit. The particular orientation can depend e.g. on space and distance considerations as well as utilization of hydrostatic pressures for different purposes.

In a second aspect the present invention discloses a method for perfusion culture of cells, comprising the steps of:

a) providing a system 1;31;51 as described above;

b) adding cell culture medium and cells to the bioreactor 2;32;52;

c) cultivating cells in the bioreactor under agitation;

d) during cultivation operating the reciprocating pump 7;37;57 to i) withdraw fluid from the bioreactor via the length of tubing 11;41;61, the branch point 10;40;60 and the inlet check valve 8;38;58 to the retentate inlet end 4;34;54 of the filter unit 3;33;53 and to ii) return fluid from the retentate outlet end 5;35;55 of the filter unit via the outlet check valve 9;39;59, the branch point 10;40;60 and the length of tubing 11;41;61 to the bioreactor 2;32;52 and;

e) withdrawing a permeate from the permeate outlet port 6;36;56.

In some embodiments the method comprises adding at least one fluid, such as a cell culture medium, to the bioreactor during cultivation. This has the advantage that culture liquid removed via the filter unit can be replenished and that fresh nutrients and other reagents can be supplied to the culture.

In certain embodiments the filter unit comprises a microfiltration membrane and the permeate comprises a target substance expressed by the cells. This allows for continuous harvest of the target substance, which can be e.g. a protein such as an immunoglobulin.

In some embodiments the filter unit comprises an ultrafiltration membrane and a target substance expressed by the cells is retained in the retentate and returned to the bioreactor.

This allows for continuous removal of toxic or otherwise undesirable low molecular weight waste products/metabolites from the cell culture, while the target substance, e.g. a protein such as an immunoglobulin, can be harvested from the culture at the end of the cultivation.

In certain embodiments the method comprises controlling at least one of the reciprocating pump and the inlet control valve to keep the pressure reading from the inlet pressure transducer within a preset range during the outward strokes of the reciprocating pump. The controlling may be achieved either manually, e.g. from a manometer reading by manual adjustment of the valve or by a control unit according to signals received from the pressure transducer. The advantage of this method is that the backflushing of the filter unit due to the negative pressure generated by the outward stroke can be controlled and optimized to give an efficient cleaning of the membrane and optionally a minimal dilution of the retentate with backflushed permeate. It is also possible to control the pressure according to more complex algorithms, e.g. producing desirable pressure versus time profiles during the outward strokes.

In some embodiments the method comprises calculating a transmembrane pressure from data provided by the inlet and outlet pressure transducers or from at least one of the inlet and outlet pressure transducers and the permeate pressure transducer and controlling at least one of the reciprocating pump, the permeate pump and the inlet and outlet control valves to keep the transmembrane pressure between preset upper and lower limits. This has the advantage that mass transport across the filter membrane can be maximized and fouling and concentration polarization can be minimized. It is also possible to control the pressure according to more complex algorithms, e.g. producing desirable transmembrane pressure versus time profiles during both the outward and inward strokes.

In some embodiments the method comprises keeping the transmembrane pressure within a first range during the outward stroke of the reciprocating pump and within a second range during the inward stroke of the reciprocating pump.

In certain embodiments the method comprises operating the permeate pump 50 in a backward direction to produce a backflush of the filter membrane. The permeate pump may be the sole source of the backflush or the permeate pump may be thus operated during the outward stroke of the reciprocating pump to assist in the backflush and to create desirable pressure/flow profiles during the backflush cycle. The permeate pump may be controlled by the one or more control units 47, according to input data from e.g. the permeate pressure transducer 49.

When the system is composed of single-use components, it is economically feasible to discard all the components after use. The system described above is particularly suitable for single-use application, but it is also possible to use conventional alternating tangential flow systems in a single-use mode.

In a third aspect the invention discloses a pre-sterilized system for perfusion culture of cells, which comprises:
a) at least one bioreactor (2;32;52);
b) at least one reciprocating pump (7;37;57)
c) at least one filter unit (3) fluidically connected to the reciprocating pump and fluidically connected to the bioreactor via at least one aseptic connector.

By providing the system as a closed and contained pre-sterilized system, the assembly, cleaning and sterilization of a conventional alternating tangential flow system, as well as the respective validation of these processes, is omitted. Further, the complexity in the connection of a conventional alternating tangential flow system, which is to be sterilized by autoclaving or steaming before establishing the fluidic connection to an already sterilized (disposable) bioreactor, is significantly reduced by providing a pre-sterilized system as readily available aseptic connectors, such as e.g. ReadyMate (GE Healthcare), can be used.

In some embodiments the pre-sterilized system is assembled from at least two pre-sterilized modules via one or more aseptic connectors. A pre-sterilized single-use alternating tangential flow filtration system may be assembled at the point of use from pre-sterilized single-use modules building such a system by using aseptic connectors at respective interfaces in between the modules, compare FIG. 4. Hereby, higher flexibility is achieved in sizing the capacity of the pre-sterilized single-use alternating tangential flow filtration system by selecting and assembling filter size and pump size or other components to match the capacity and performance suitable to the bioreactor and process to be served.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. It is to be noted that elements from different embodiments and aspects may be combined to form new embodiments.

The invention claimed is:

1. A system for perfusion culture of cells comprising:
a) at least one bioreactor;
b) at least one filter unit comprising a retentate inlet end, a retentate outlet end that is on the opposite end of the at least one filter unit, and at least one permeate outlet port;
c) at least one reciprocating pump fluidically connected to the retentate inlet end,
wherein said retentate inlet end is fluidically connected to said at least one bioreactor via an inlet check valve arranged to allow flow in the direction from the at least one bioreactor to the retentate inlet end and to block flow in the reverse direction, and wherein said retentate outlet end is fluidically connected to said at least one bioreactor via an outlet check valve arranged to allow flow in the direction from the retentate outlet end to the at least one bioreactor and to block flow in the reverse direction; and
wherein said inlet and outlet check valves are each fluidically connected to a tubing branch point, which is further connected to the at least one bioreactor via a length of tubing.

2. The system according to claim 1, wherein said length of tubing has an inner volume lower than or equal to 50% of the stroke volume of the at least one reciprocating pump.

3. The system according to claim 1, further comprising an inlet control valve between said inlet check valve and said branch point.

4. The system according to claim 1, further comprising an outlet control valve between said outlet check valve and said branch point.

5. The system according to claim 1, further comprising an inlet pressure transducer arranged to measure the pressure at said retentate inlet end.

6. The system according to claim 1, wherein the at least one reciprocating pump is a fluid-driven diaphragm pump and the system comprises a drive fluid pressure transducer arranged to measure a drive fluid pressure in the at least one reciprocating pump.

7. The system according to claim 5, further comprising at least one control unit, arranged to control at least one of the at least one reciprocating pump, an inlet control valve, and an outlet control valve depending on pressure data received from said inlet pressure transducer.

8. The system according to claim 7, wherein the at least one control unit is arranged to control at least one of the inlet control valve and the at least one reciprocating pump depending on pressure data received from said inlet pressure transducer.

9. The system according to claim 1, further comprising a permeate pump and a permeate pressure transducer.

10. The system according to claim 1, wherein said at least one filter unit is a hollow fiber cartridge or a flat sheet cassette.

11. The system according to claim 1, wherein said at least one bioreactor comprises an inflatable flexible bag resting on a movable support, and wherein the length of tubing is a flexible length of tubing.

12. The system of claim 1, wherein the at least one filter unit is fluidically connected to the bioreactor via at least one aseptic connector.

13. A method for perfusion culture of cells, comprising:
a) providing a system according to claim 1;
b) adding cell culture medium and cells to said at least one bioreactor;
c) cultivating cells in said at least one bioreactor under agitation;
d) operating, during cultivation, said at least one reciprocating pump to i) withdraw fluid from said at least one bioreactor via said length of tubing, said branch point and said inlet check valve to said retentate inlet end of said at least one filter unit and to ii) return fluid from said retentate outlet end of said at least one filter unit via said outlet check valve, said branch point and said length of tubing to said at least one bioreactor and;

e) withdrawing a permeate from at least one permeate outlet port.

14. The method according to claim 13, further comprising adding at least one fluid to the at least one bioreactor during cultivation.

15. The method according to claim 13, wherein the at least one filter unit comprises a microfiltration membrane and wherein the permeate comprises a target substance expressed by the cells.

16. The method according to claim 13, wherein the at least one filter unit comprises an ultrafiltration membrane and wherein a target substance expressed by the cells is retained in the retentate and returned to the at least one bioreactor.

17. The method according to claim 13, further comprising controlling at least one of the at least one reciprocating pump and an inlet control valve to keep the pressure reading from an inlet pressure transducer within a preset range during outward strokes of the at least one reciprocating pump.

18. The method according to claim 13, further comprising calculating a transmembrane pressure from data provided by an inlet pressure transducer and an outlet pressure transducer; and controlling at least one of the at least one reciprocating pump and the inlet and outlet control valves to keep the transmembrane pressure between preset upper and lower limits.

19. The method according to claim 18, wherein the trans-membrane pressure is kept within a first range during outward strokes of the at least one reciprocating pump and within a second range during inward strokes of the at least one reciprocating pump.

20. The method according to claim 13, further comprising operating a permeate pump in a direction to produce a back-flush of a filter membrane.

21. A system for perfusion culture of cells comprising: a) at least one bioreactor; b) at least one filter unit comprising a retentate net end, a retentate outlet end that is on the opposite end of the at least one filter unit, and at least one permeate outlet port; wherein the at least one filter unit is fluidically connected to the at least one bioreactor via at least one aseptic connector, and c) at least one reciprocating pump fluidically connected to the retentate net end, wherein said retentate net end is fluidically connected to said at least one bioreactor via an net check valve arranged to allow flow in the direction from the at least one bioreactor to the retentate net end and to block flow in the reverse direction, and wherein said retentate outlet end is fluidically connected to said at least one bioreactor via an outlet check valve arranged to allow flow in the direction from the retentate outlet end to the at least one bioreactor and to block flow in the reverse direction; and wherein said net and outlet check valves are each fluidically connected to a tubing branch point, which is further connected to the at least one bioreactor via a length of tubing.

22. The system according to claim 21, wherein said length of tubing has an inner volume lower than or equal to 50% of the stroke volume of the at least one reciprocating pump.

23. The system according to claim 21, further comprising an inlet control valve between said inlet check valve and said branch point.

24. The system according to claim 21, further comprising an outlet control valve between said outlet check valve and said branch point.

25. The system according to claim 21, further comprising an inlet pressure transducer arranged to measure the pressure at said retentate inlet end.

26. The system according to claim 21, wherein the at least one reciprocating pump is a fluid-driven diaphragm pump and the system comprises a drive fluid pressure transducer arranged to measure a drive fluid pressure in the at least one reciprocating pump.

27. The system according to claim 25, further comprising at least one control unit, arranged to control at least one of the least one reciprocating pump, an net control valve, and an outlet control valve depending on pressure data received from said net pressure transducer.

28. The system according to claim 27, wherein the at least one control unit is arranged to control at least one of the net control valve and the at least one reciprocating pump depending on pressure data received from said inlet pressure transducer.

29. The system according to claim 21, further comprising a permeate pump and a permeate pressure transducer.

30. The system according to claim 21, wherein said at least one filter unit is a hollow fiber cartridge or a flat sheet cassette.

31. The system according to claim 21, wherein said at least one bioreactor comprises an inflatable flexible hag resting on a movable support, and wherein the length of tubing is a flexible length of tubing.

32. A method for perfusion culture of cells, comprising: f) providing a system according to claim 21; g) adding cell culture medium and cells to said at least one bioreactor; h) cultivating cells in said at least one bioreactor under agitation; i) operating, during cultivation, said at least one reciprocating pump to iii) withdraw fluid from said at least one bioreactor via said length of tubing, said branch point and said net check valve to said retentate net end of said at least one filter unit and to iv) return fluid from said retentate outlet end of said at least one filter unit via said outlet check valve, said branch point and said length of tubing to said at least one bioreactor and; j) withdrawing a permeate from at least one permeate outlet port.

33. The method according to claim 32, further comprising adding at least one fluid to the at least one bioreactor during cultivation.

34. The method according to claim 32, wherein the at least one filter unit comprises a microfiltration membrane and wherein the permeate comprises a target substance expressed by the cells.

35. The method according to claim 32, wherein the at least one filter unit comprises an ultrafiltration membrane and wherein a target substance expressed by the cells is retained in the retentate and returned to the at least one bioreactor.

36. The method according to darn 32, further comprising controlling at least one of the at least one reciprocating pump and an net control valve to keep the pressure reading from an net pressure transducer within a preset range during outward strokes of the at least one reciprocating pump.

37. The method according to claim 32, further comprising calculating a transmembrane pressure from data provided by an net pressure transducer and an outlet pressure transducer; and controlling at least one of the at least one reciprocating pump and the net and outlet control valves to keep the transmembrane pressure between preset upper and lower limits.

38. The method according to claim 37, wherein the transmembrane pressure is kept within a first range during outward strokes of the at least one reciprocating pump and within a second range during inward strokes of the at least one reciprocating pump.

39. The method according to claim 32, further comprising operating a permeate pump in a direction to produce a back-flush of a filter membrane.

* * * * *